US009720065B2

(12) United States Patent
Rapoport et al.

(10) Patent No.: US 9,720,065 B2
(45) Date of Patent: Aug. 1, 2017

(54) METHOD FOR PROVIDING HIGH RESOLUTION, HIGH CONTRAST FUSED MRI IMAGES

(75) Inventors: Uri Rapoport, Moshav Ben Shemen (IL); Ditza Auerbach, Aseret (IL)

(73) Assignee: ASPECT MAGNET TECHNOLOGIES LTD., Shoham (IL)

( * ) Notice: Subject to any disclaimer, the term of this patent is extended or adjusted under 35 U.S.C. 154(b) by 834 days.

(21) Appl. No.: 13/877,553

(22) PCT Filed: Oct. 6, 2011

(86) PCT No.: PCT/IL2011/000795
§ 371 (c)(1),
(2), (4) Date: May 22, 2014

(87) PCT Pub. No.: WO2012/046241
PCT Pub. Date: Apr. 12, 2012

(65) Prior Publication Data
US 2015/0077105 A1    Mar. 19, 2015

Related U.S. Application Data

(60) Provisional application No. 61/390,196, filed on Oct. 6, 2010.

(51) Int. Cl.
*G01R 33/565* (2006.01)
*G01N 24/08* (2006.01)
(Continued)

(52) U.S. Cl.
CPC ......... *G01R 33/565* (2013.01); *G01N 24/082* (2013.01); *G01R 33/38* (2013.01); *G01R 33/5608* (2013.01); *G01N 24/085* (2013.01)

(58) Field of Classification Search
CPC .. G01R 33/38; G01R 33/5608; G01R 33/565; G01R 33/56; G01N 24/085
(Continued)

(56) References Cited

U.S. PATENT DOCUMENTS 5,332,968 A    7/1994  Brown
6,804,384 B2   10/2004 Lowen
(Continued)

FOREIGN PATENT DOCUMENTS

EP    0637387 B1 * 10/1997  ............ G01R 33/56
JP    2005-152114    6/2005
(Continued)

OTHER PUBLICATIONS

Kumar, Y. Kiran. "Comparison of fusion techniques applied to preclinical images: fast discrete curvelet transform using wrapping technique & wavelet transform." Journal of Theoretical and Applied Information Technology 5.6 (2009): 668-673.*
(Continued)

*Primary Examiner* — Melissa Koval
*Assistant Examiner* — Rishi Patel
(74) *Attorney, Agent, or Firm* — Pearl Cohen Zedek Latzer Baratz LLP (57) ABSTRACT

This present invention relates to an MRI scanning assembly and a method for fusing MRI images of a target thereby generating and providing high resolution, high contrast fused MRI images. The MRI images of the target are generated by different MRI devices operating at different magnetic field intensities. A method is also described for fusing MRI images generated by an MRI device operating with different operational parameters and operational protocols.

12 Claims, 7 Drawing Sheets

(51) Int. Cl.
*G01R 33/38* (2006.01)
*G01R 33/56* (2006.01)

(58) Field of Classification Search
USPC .................................................. 324/307, 309
See application file for complete search history.

(56) References Cited

U.S. PATENT DOCUMENTS

| | | | |
|---|---|---|---|
| 7,145,336 B2 | 12/2006 | Brown | |
| 7,400,147 B2* | 7/2008 | Rapoport | G01R 33/383 324/318 |
| 8,807,084 B2 | 8/2014 | Rapoport et al. | |
| 8,851,018 B2 | 10/2014 | Rapoport et al. | |
| 8,896,310 B2 | 11/2014 | Rapoport | |
| 2003/0193332 A1* | 10/2003 | Shah | G01R 33/482 324/300 |
| 2003/0193515 A1 | 10/2003 | Hill et al. | |
| 2005/0240098 A1* | 10/2005 | Zhong | G01R 33/285 600/410 |
| 2006/0257027 A1 | 11/2006 | Hero et al. | |
| 2008/0019919 A1 | 1/2008 | Rustum et al. | |
| 2008/0144910 A1 | 6/2008 | Weissenborn | |
| 2010/0016936 A1 | 1/2010 | Stevenson et al. | |
| 2011/0162652 A1 | 7/2011 | Rapoport | |
| 2011/0186049 A1 | 8/2011 | Rapoport | |
| 2011/0234347 A1 | 9/2011 | Rapoport | |
| 2011/0304333 A1 | 12/2011 | Rapoport | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0119742 A1 | 5/2012 | Rapoport | |
| 2013/0079624 A1 | 3/2013 | Rapoport | |
| 2013/0109956 A1 | 5/2013 | Rapoport | |
| 2013/0237803 A1 | 9/2013 | Rapoport | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051975 A1* | 2/2014 | Rapoport | A61B 6/5247 600/411 |
| 2014/0051976 A1 | 2/2014 | Rapoport et al. | |
| 2014/0099010 A1 | 4/2014 | Rapoport et al. | |
| 2014/0103927 A1 | 4/2014 | Rapoport | |
| 2014/0117989 A1 | 5/2014 | Rapoport | |
| 2014/0128725 A1 | 5/2014 | Rapoport et al. | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0257081 A1 | 9/2014 | Rapoport | |
| 2014/0266203 A1 | 9/2014 | Rapoport et al. | |
| 2014/0300358 A1 | 10/2014 | Rapoport | |
| 2014/0378821 A1 | 12/2014 | Rapoport et al. | |
| 2014/0378825 A1 | 12/2014 | Rapoport et al. | |
| 2015/0059655 A1 | 3/2015 | Rapoport | |
| 2015/0065788 A1 | 3/2015 | Rapoport | |
| 2015/0077105 A1 | 3/2015 | Rapoport et al. | |

FOREIGN PATENT DOCUMENTS

| | | |
|---|---|---|
| JP | 2007-532259 | 10/2005 |
| JP | 2011-527222 | 10/2011 |
| WO | WO2005/101045 | 10/2005 |
| WO | WO2010/004427 | 1/2010 |

OTHER PUBLICATIONS

Jolliffe, Ian. Principal component analysis. John Wiley & Sons, Ltd, 2002.*

International Preliminary Report on Patentability dated Jul. 8, 2013 in corresponding International Application No. PCT/IL11/000795.
International Search Report and Written Opinion dated Mar. 21, 2012 in corresponding International Application No. PCT/IL2011/000795.
Lin et al., Optically tunable nanoparticle contrast agents for early cancer detection: model-based analysis of gold nahoshells, Journal of Biomed. Opt. 10(6), 064035 (2005).
Glunde et al., "Will magnetic resonance imaging (MRI)-based contrast agents for molecular receptor imaging make their way into the clinic?" *J. Cell. Mol. Med.* 12(2), 187 (2008) pp. 1-2.
Japanese Office Action for JP Application No. 2013-532318 dated May 6, 2016.
Notice of Allowance for JP Application No. 2013-532318 dated Sep. 6, 2016.
Rapoport, Uri, "RF Shielding Conduit in an MRI Closure Assembly", co-pending U.S. Appl. No. 14/574,785, filed Dec. 18, 2014.
Aspect Imaging Ltd., "System and Method for Generating Invasively Hyperpolarized Images", co-pending U.S. Appl. No. 14/556,682, filed Dec. 1, 2014.
Aspect Imaging Ltd., "System and Method for Generating Invasively Hyperpolarized Images", co-pending U.S. Appl. No. 14/556,654, filed Dec. 1, 2014.
Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.
Aspect Imaging Ltd., "Foamed Patient Transport Incubator", co-pending U.S. Appl. No. 14/531,289, filed Nov. 3, 2014.
Aspect Imaging Ltd., "Mechanical Clutch for MRI", co-pending U.S. Appl. No. 14/611,379, filed Feb. 2, 2015.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable Nmr Probe Cassette and Methods Thereof", co-pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.
Aspect Imaging Ltd, "MRI—Incubator's Closure Assembly", co-pending U.S. Appl. No. 14/539,442, filed Nov. 12, 2014.
Aspect Imaging Ltd., "Shutting Assembly for Closing an Entrance of an MRI Device", co-pending U.S. Appl. No. 14/540,163, filed Nov. 13, 2014.
Aspect Imaging Ltd., "Cage in an MRD with a Fastening/Attenuating System", co-pending U.S. Appl. No. 14/527,950, filed Oct. 30, 2014.
Aspect Imaging Ltd., "Means for Operating an MRI Device Within a RF-Magnetic Environment", co-pending U.S. Appl. No. 14/596,320, filed Jan. 14, 2015.
Aspect Imaging Ltd., "Means and Method for Operating an MRI Device Within a RF-Magnetic Environment", co-pending U.S. Appl. No. 14/596,329, filed Jan. 14, 2015.
Aspect Imaging Ltd., "CT/MRI Integrated System for the Diagnosis of Acute Strokes and Methods Thereof", co-pending U.S. Appl. No. 14/598,517, filed Jan. 16, 2015.
Aspect Imaging Ltd., "RF Automated Tuning System Used in a Magnetic Resonance Device and Methods Thereof", co-pending U.S. Appl. No. 14/588,741, filed Jan. 2, 2015.
Aspect Imaging Ltd., "A Method For Providing High Resolution, High Contrast Fused MRI Images", co-pending U.S. Appl. No. 13/877,553, filed Apr. 3, 2013.

(56) References Cited

OTHER PUBLICATIONS

Aspect Imaging Ltd., "A Method For Manipulating The MRI's Protocol of Pulse-Sequences", co-pending U.S. Appl. No. 14/070,695, filed Nov. 4, 2013.

* cited by examiner

Combining Low Resolution with High Resolution (same slice)

METHOD FOR PROVIDING HIGH RESOLUTION, HIGH CONTRAST FUSED MRI IMAGES

FIELD OF THE INVENTION

The present invention relates an MRI assembly and method for providing high resolution fused MRI images of a target.

BACKGROUND OF THE INVENTION

The following prior art is believed to be the current status of the art:

U.S. Pat. No. 5,332,968 describes an apparatus and method for producing a single color coded composite image from a plurality of multi-parameter magnetic resonance image sets. However, this prior art does not relate to generating multi-colored images.

EP 0 637 387 B1 describes a method and apparatus for color coding a plurality of images obtained at a plurality of pulse sequences. However, in the prior art method the monochrome colors are determined empirically according to an average pixel value of user identified regions of interest and according to required output color of these regions.

U.S. Pat. No. 6,804,384 B2 describes color magnetic resonance imaging using both a magnetic resonance property and a function of the magnetic resonance property. This prior art system only includes determined results from a single pulse sequence.

U.S. Pat. No. 7,145,336 B2 describes a system and method for creating and manipulating one or more color-coded magnetic resonance images. This prior art system does not relate to combining MRI images from different MRI devices taken at different magnetic field intensities. Furthermore it does not deal with the issue of images with varying resolution explicitly.

"Comparison of Fusion Techniques Applied to Preclinical Images: Fast Discrete Curvelet Transform Using Wrapping Technique & Wavelet Transform", by Y. Kiran Kumar, J. of Theoretical & Applied Information Technology, 2005-2009, JATIT, pp 668-673 describes a method for fusing of registered images. However, the prior art system does not relate to different image resolutions and does not consider fusing MRI images generated by more than one MRI device.

However, the prior art MRI devices and methods for generating high contrast images with high spatial resolution of high signal to noise ratio (SNR) are time consuming and/or require very specific contrast agents. Thus, there is a long felt and hitherto unmet requirement for providing high contrast images with high spatial resolution and high SNR.

SUMMARY OF THE INVENTION

The present invention relates an MRI scanning assembly and method for providing high contrast images of several colors with high spatial resolution by fusing MRI images of a target taken at different magnetic field strengths.

In addition, the present invention relates to an MRI scanning device for generating a plurality of MRI images of a target, wherein each MRI scanned image is associated with at least one member of a group of MRI device parameters, such as pixel size, dwell time, T1-weighted scan protocols and T2-weighted scan protocols.

It is known in the art, that high resolution MRI images have increased noise, since the noise increases as smaller voxels are imaged. Therefore, in MRI systems, there is often a trade-off between high SNR and high-resolution in terms of image acquisition of a particular tool. The present invention describes systems and methods for generating high resolution MRI images with high SNR by fusing MRI images generated at different resolutions and contrast and producing an enhanced single image having a superior image quality than the MRI individual images.

Typically, MRI devices which have a relatively low intensity magnetic field, of less than 1.0 Tesla, produce high resolution images with low Signal-to-Noise Ratios (SNR). However, MRI devices which have a relatively high intensity magnetic field, in the higher than 3.0 Tesla, produce high resolution images with high Signal-to-Noise Ratios (SNR).

Furthermore, tissue contrast can be considered separately from image resolution, when referring to relatively large tissue masses. The contrast is controlled by the imaging mode and can be selectively enhanced by the use of contrast agents and by reducing noise sources. In addition, fusing MRI images generated at different resolutions and contrast produces an enhanced single image having a superior image quality than the MRI individual images.

MRI devices are used for a variety of diagnostic purposes, for example, to detect and to determine the location of pathological tissues such as cancers. MRI devices are used to detect cancers that would otherwise be difficult to diagnose and to indicate the precise location and size of tumors. MRI devices provide a non-invasive method for conducting pathological examinations and studies.

In addition, MRI devices are also applicable for non-pathological purposes for providing non-invasive examinations of targets for industrial purposes. For example, MRI device are applicable for analyzing and examining non-invasively the compositions of food products for content-checking purposes and searching and investigating fluids.

MRI devices which have a relatively low intensity magnetic field, less than 1.0 Tesla, produce high resolution images with low Signal-to-Noise Ratios (SNR). MRI devices which have a relatively high intensity magnetic field, in the range of 3 Tesla and above, can produce high resolution images but often lack contrast for some tissues of interest In order to improve contrast and reducing noise in high resolution MRI images, the present invention exploits the property of high contrast obtainable in low intensity magnetic fields. The method adopted is combining and fusing MRI images of a target generated by an MRI device operating with a low intensity magnetic field and MRI images generated by an MRI device operating with a high intensity magnetic field. By combining and fusing the images thereof, MRI images with low noise and improved contrast between tissue masses are obtained.

Additionally, the present invention also generates an enhanced MRI image by introducing a colored image.

It is appreciated that an MRI image of a target includes many image slices.

Although the description below relates to a single MRI image slice, this is by example only. The MRI scan measurements and analysis are performed for a plurality of slices of the target.

There is provided in accordance with a preferred embodiment of the present invention an MRI scanning assembly characterized by an MRI scanning device operating at a first magnetic field intensity and generating a first plurality of MRI images of a target, an MRI scanning device operating at a second magnetic field intensity and generating a second plurality of MRI images of the target, and a processing unit configured to fuse the first plurality of MRI images and the second plurality of MRI images to generate a clear image representation of at least a portion of the target.

There is further provided in accordance with a preferred embodiment of the present invention a method for fusing MRI images of a target including providing an MRI scanning device operating at a first magnetic field intensity providing an MRI scanning device operating at a second magnetic field intensity, generating a first plurality of MRI images of the target by the MRI scanning device operating at a first magnetic field intensity, generating a second plurality of MRI images of the target by the MRI scanning device operating at a second magnetic field intensity, and configuring a processing unit to fuse the first plurality of MRI images and the second plurality of MRI images to generate a clear image representation of at least a portion of the target.

Further in accordance with a preferred embodiment of the present invention, the first magnetic field intensity is less than 1.5 Tesla and the second magnetic field intensity is greater than 5 Tesla.

Still further in accordance with a preferred embodiment of the present invention the target is selected from the group consisting of a group of cancerous cell, at least one anatomical organ, at least one cancerous anatomical organ and any combination thereof.

Additionally in accordance with a preferred embodiment of the present invention the MRI scanning device operating at the first magnetic field intensity includes an MRD device.

Moreover in accordance with a preferred embodiment of the present invention further including an MRI selector for selecting the MRI scanning device.

Additionally, in accordance with a preferred embodiment of the present invention further including an image display unit for generating and displaying the at least the portion of the target.

Moreover in accordance with a preferred embodiment of the present invention including identifying at least two regions of interest in the first plurality of the MRI images of the target scanned at the first magnetic field intensity.

Further in accordance with a preferred embodiment of the present invention further including determining a monochrome level scaling factor between the at least two identified regions of interest;

Still further in accordance with a preferred embodiment of the present invention further including scaling each image of the second plurality of images of the target scanned at the second magnetic field intensity with the monochrome level scaling factor.

Further in accordance with a preferred embodiment of the present invention, generating and displaying a clear anatomic appearance of at least a portion of the target.

Additionally in accordance with a preferred embodiment of the present invention the monochrome level is selected from a grey level, a red scale, a green scale and a blue scale.

In accordance with yet another preferred embodiment of the present invention an MRI scanning assembly characterized by at least one MRI scanning device generating a plurality of MRI images of a target, each one of the plurality of MRI images is associated with at least one member of a group of MRI device parameters, and a processing unit configured to fuse at least one MRI image of the plurality of MRI images with at least remaining one of the plurality of MRI images to generate a clear image representation of at least a portion of the target.

In accordance with yet another preferred embodiment to the present invention a method for fusing MRI images of a target including: providing at least one MRI scanning device generating a plurality of MRI images of a target, each one of the plurality of MRI images is associated with at least one member of a group of MRI device parameters, generating the plurality of MRI images of the target by the at least one MRI scanning device, configuring a processing unit to fuse at least one MRI image of the plurality of MRI images with at least remaining one of the plurality of MRI images to generate a clear image representation of at least a portion of the target.

Further in accordance with a preferred embodiment of the present invention the group of MRI device parameters is selected from the group consisting of MRI scanning parameters and MRI scanning protocols and any combination thereof.

Additionally in accordance with a preferred embodiment of the present invention the group of MRI scanning parameters includes at least one of the following: pixel size and dwell time.

Moreover in accordance with a preferred embodiment of the present invention the group of MRI scanning protocols includes at least one of the following protocols: T1-weighted scan protocols and T2-weighted scan protocols.

Preferably the MRI scanning device includes an MRD device.

Further in accordance with a preferred embodiment of the present invention including an image display unit for generating and displaying the at least the portion of the target.

Still further the image representation is selected from the group consisting of an anatomic appearance and a non-anatomic appearance.

Further in accordance with a preferred embodiment of the present invention the MRI scans include MRI scans for searching and investigating fluids as well as investigating food products and industrial products.

BRIEF DESCRIPTION OF THE DRAWINGS

A preferred embodiment of the current invention is described hereinbelow with reference to the following drawings.

DETAILED DESCRIPTION OF A PREFERRED EMBODIMENT OF THE PRESENT INVENTION

Figure 1:
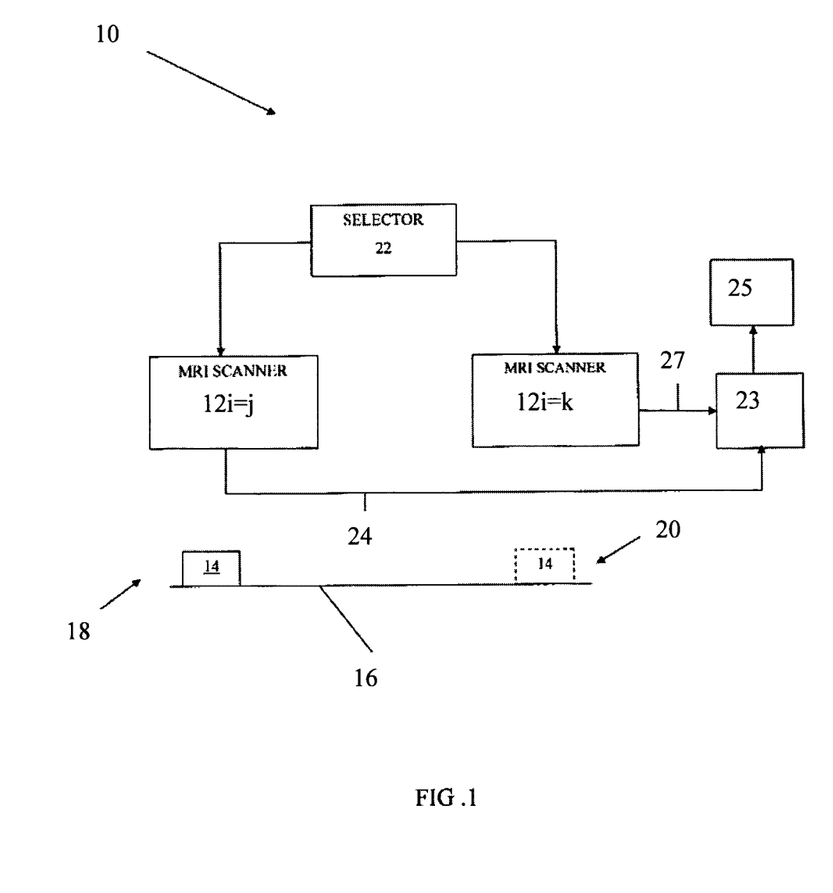
FIG. 1 shows an MRI scanning assembly for fusing scanned MRI images generated at a low magnetic field intensity and generated at a high magnetic field intensity, according to a preferred embodiment of the present invention.

Reference is now made to FIG. 1, which shows an MRI scanning assembly 10 for fusing scanned MRI images, according to a preferred embodiment of the present invention. The MRI scanning assembly 10 includes, inter alia, MRI scanning devices $12_{i=j}$ and $12_{i=k}$, where $1 \leq i \leq N$ and N is the number of MRI devices available for generating the MRI scans at different magnetic field intensities.

Typically, in the MRI scanning assembly 10, the MRI scans of a target 14 are performed at different magnetic field intensities, such that the MRI devices $12_{i=j}$ and $12_{i=k}$ scan the target 14 at a different magnetic field intensities. In order for the devices $12_{i=j}$ and $12_{i=k}$ to scan the target 14, the target 14 is located on a moving platform 16 which transports the target 14 from a scanning location 18 at the device $12_{i=j}$ to a scanning location 20 at the device $12_{i=k}$.

The MRI scanning assembly 10 also includes an MRI selector 22 which selects the MRI devices $12_{i=j}$ or $12_{i=k}$ for scanning the target 14 at the scanning locations 18 and 20, respectively. Thus, for example, the selector 22 instructs the MRI device $12_{i=j}$ to scan the target at the low magnetic field intensity.

Typically, for example, the low magnetic field intensity is in a range of approximately 0.5 Tesla to approximately 1.5 Tesla. The device $12_{i=j}$ scans the target 14 and generates a plurality of MRI target scans 24.

Following the "low-field scan", the target 14 is transported to the location 20 and the magnetic field selector 22 instructs device 12i=k to scan the target 14 at a higher magnetic field intensity scan. For example, for the "high-field scan", the high magnetic field intensity is typically in a magnetic field intensity range of approximately 3 Tesla to 16 Tesla. The device $12_{i=k}$ scans the target 14 and generates a plurality of MRI target scans 27.

It is appreciated that the MRI devices $12_{i=j}$ and $12_{i=k}$ generate a plurality of MRI scans of the target 14 at each magnetic field intensity, as required. The plurality of scans is generated by changes in the MRI device parameters, such as the pulse sequence or a scanning protocol. The pulse sequence determines the dynamics of the magnetic moments and therefore determines the measured signal intensity.

On completion of the respective MRI scans of the target 14, the MRI devices $12_{i=j}$ and $12_{i=k}$ transfer the scanned MRI data 24 and 27, respectively, to a processing unit 23 for processing, analyzing and interpretation by an operator. The processing unit 23 allows the operator to reconstruct the MRI scans, which are taken in "k-space" and convert the MRI images into "real-space". The analysis of the reconstructed MRI scans is conducted in accordance with an analysis tool, as discussed below. The operator manually or with the aid of a computing device (semi-automatically), analyzes the reconstructed MRI scans. The analysis involves, for example, the operator outlining and segmenting a region of the reconstructed scan, such as an organ or a pathological feature. In addition, the operator, typically, makes measurements of the segmented region, such as the volume of region and the average signal strength.

The processing unit 23 forwards the results of the analysis to an MRI image display device 25.

Alternatively, the plurality of MRI scans 24 and 27 are generated by a single MRI scanning device $12_{i=1}$, which includes a typical device is the MRD scanning device, as described in U.S. Pat. No. 7,400,147, which is owned by the owner of the present application and is incorporated herein by reference in its entirety.

In the single MRI device. different MRI images are generated by using different device parameters, such as pixel size and dwell time and different scanning parameters, such as a T1-weighted scanning protocol and a T2-weighted protocol.

Figure 2A:
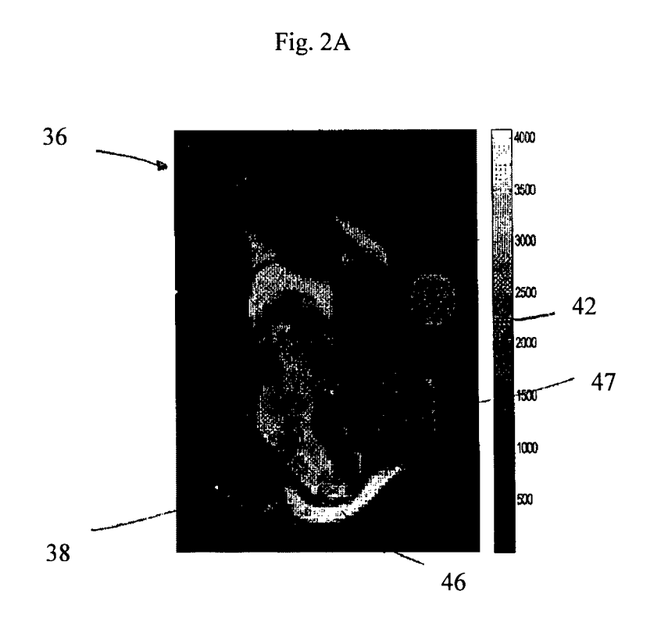
FIGS. 2A and 2B compare a single slice generated from MRI scans of the rodent at the low magnetic field intensity and the high magnetic field intensity, respectively, in accordance with a preferred embodiment of the present invention.
Figure 2B:
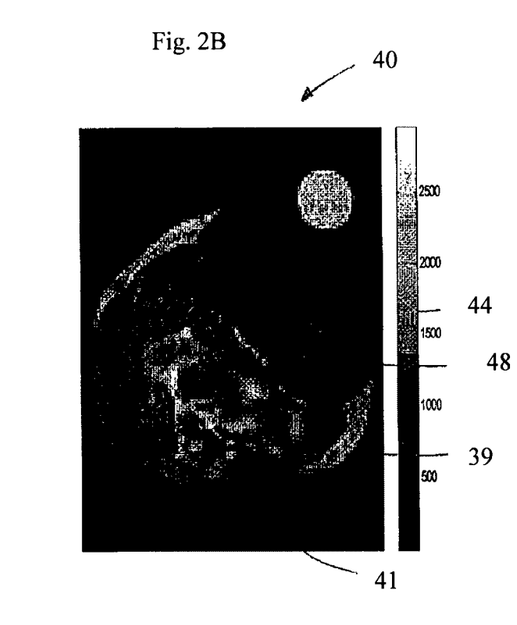

FIGS. 2A and 2B compares the MRI the resolution of MRI images obtained at a magnetic field intensity of approximately 7 Tesla with the resolution of MRI images obtained at a magnetic field intensity of approximately 1 Tesla, respectively, in accordance with a preferred embodiment of the present invention;

Reference is now made to FIGS. 2A and 2B, which compares generated MRI scans of the rodent at the low magnetic field intensity and the high magnetic field intensity, respectively, in accordance with a preferred embodiment of the present invention. FIG. 2A shows a scan slice 36 of the small rodent with a tumor 38, taken at a magnetic field intensity of approximately 1 Tesla. FIG. 2B shows a scan slice 40 of the rodent with a tumor 39 at a magnetic field intensity of approximately 7 Tesla, at a different slice of the rodent.

The scan slices 36 and 40 in FIGS. 2A and 2B, respectively, are not the same scan slice. Thus, the scan slices 36 and 40 are non-coherent. The MRI slices 36 and 40 do not include the same content and portion of the rodent. Thus, pixel-wise registration is not possible. The low resolution scan includes a higher SNR level than that of the high resolution scan (FIG. 2A). In order to enhance and improve the contrast between tissue masses of the high resolution scan, preferably, the low resolution scan (FIG. 2B) is fused with the high resolution scan of FIG. 2A thereby enhancing the contrast in FIG. 2B.

The MRI scan in FIG. 2A is a low-resolution image of approximately 300 µM pixel size and with high contrast between certain tissues. FIG. 2A also shows a corresponding grey level scale 42. FIG. 2B shows a high resolution scan of approximately 100 µM resolution with a high SNR and low contrast between the corresponding high contrast tissues of FIG. 2A and a corresponding grey level scale 44.

If, for example, the operator wishes to improve the contrast of a tumor area 41 (FIG. 2B), relative to the surrounding regions, thereby distinguishing and classifying the tumour area 41. The operator decides to enhance the contrast of the tumor area 41 and selects a corresponding area 38 in FIG. 2A.

In operation, the operator and/or processing unit 23 identifies two corresponding regions of interest in FIGS. 2A and 2B that are required to be enhanced in FIG. 2B. For example, the operator and/or processing unit 23 selects the tumor 38 and a fatty white portion 46 in FIG. 2A. Similarly, preferably, the operator and/or processing unit selects corresponding regions 41 and 39 (white region) in FIG. 2B.

In operation, a tissue (or tissues) which require enhancing the contrast thereof, is selected. The entire tissue region thereof is identified, typically, by a segmentation algorithm based on a previously defined seed voxel, as is known in the art. It is appreciated that the tissue region can also be identified manually by the operator. This identification procedure is performed separately for the images 36, (FIG. 2A) and 40 (FIG. 2B), since the images 36 and 40 cannot be registered. The images 36 and 40 are MRI images of different slices of the target 14. Now a reference region must be segmented in each of the images 3A and 3B. A reference region, such as a marker reference or a tissue reference, such as muscle portion 47 in FIG. 2A and a muscle portion 48 in FIG. 2B is identified and selected. It is appreciated that the reference tissues 47 and 48 are selected since these reference tissues images appear relatively similar in both spatial extent and in terms of signal strength.

It is appreciated that for determining the reference regions the segmentation need not be accurate and does not have to include the entire spatial area of "reference object". For each image, the reference object is used to generate a mean reference signal strength by averaging the signals of its included voxels.

For the MRI scan images 36 and 40, a ratio between the mean grey levels of the segment to be enhanced with a reference segment is calculated from:

Ratio_1=mean (segment 38, image 1)/mean(ref segment 47 im 1, Image 1), wherein im 1 is image 36 in FIG. 2A.

For the MRI scan image 40, a second ratio is calculated as a mean of the grey values:

Ratio_2=mean(segment 41, image 2)/mean(ref segment 48 im 2, Image 2), wherein im 2 is image 46 in FIG. 2A.

From FIG. 2A, Ratio_1 is approximately 1.8 and from FIG. 2b, Ratio_2 is approximately 1.

A Scaling Factor SF is calculated from:

SF=RATIO_1/RATIO_2.

Based on the mean grey values determined for the segments 36 and 40, SF is determined to be approximately 1.8 for the tumor segment.

Figure 3A:
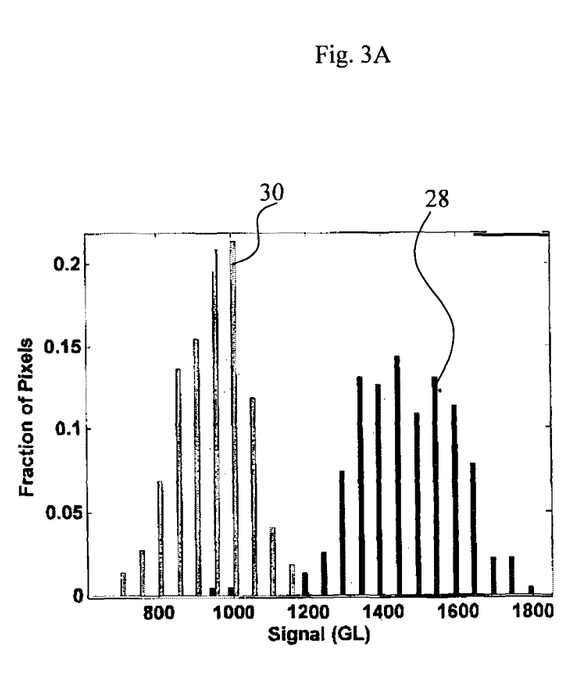
FIGS. 3A and 3B compares histograms of MRI images of the target taken at a high magnetic field intensity of approximately 1 Tesla and MRI images taken at a magnetic field intensity of approximately 7 Tesla, respectively, in accordance with a preferred embodiment of the present invention.
Figure 3B:
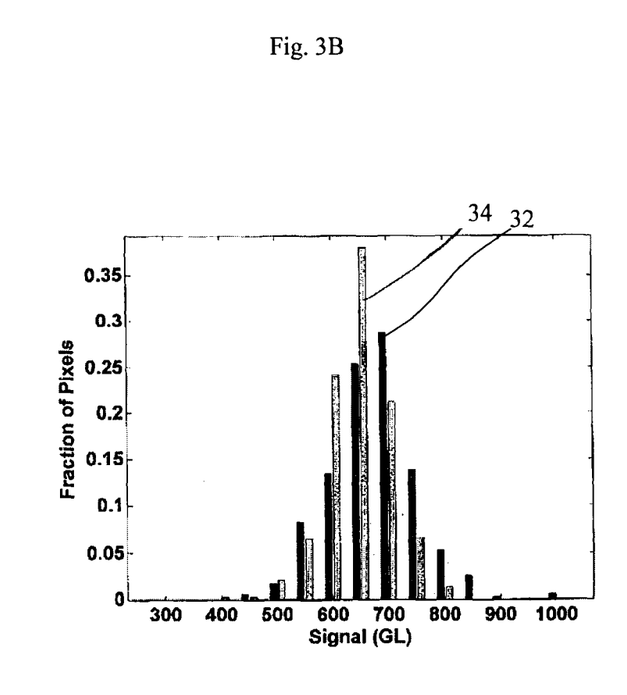
Figure 4A:
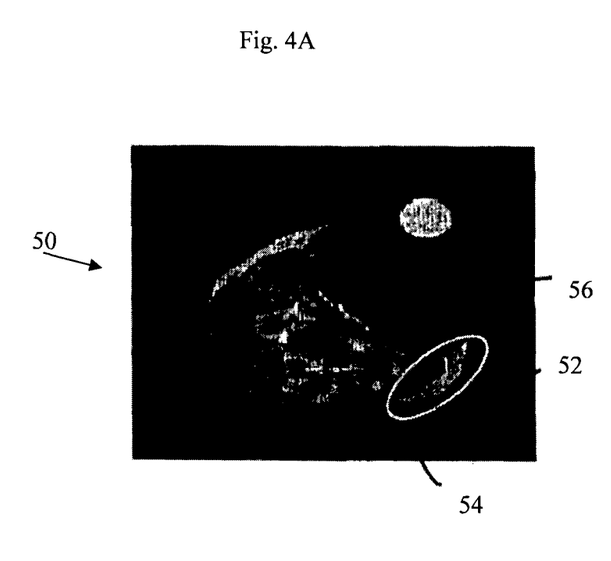
FIGS. 4A and 4B compares the original slice from the high field MRI scan with the enhanced MRI scan, respectively, in accordance with a preferred embodiment of the present invention.
Figure 4B:
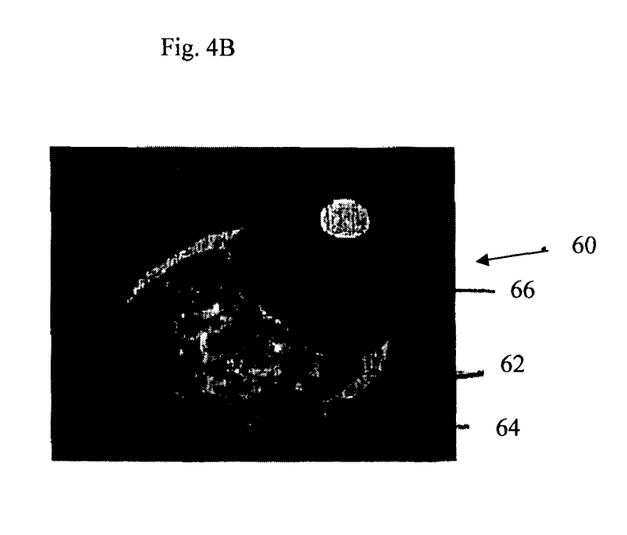

The grey values of the voxels included in segment 41 of the MRI scan image shown in 40 of FIG. 2B will be scaled by a value of 1.8 to form an enhanced high resolution as in FIG. 4B. Similar scaling is performed on other high contrast segments of image 36 of FIG. 2A. Reference is now made to FIGS. 3A and 3B, which compare histograms of MRI images of the target taken at a low magnetic field intensity of approximately 1 Tesla and MRI images taken at a high magnetic field intensity of approximately 7 Tesla, respectively, in accordance with a preferred embodiment of the present invention.

In FIG. 3A, the pixel populations of the image 36 are shown as a function of the Grey Level (GL) for two different portions of the rodent in the low-field scan. In FIG. 3A, the grey level histograms for a tumor 38 (FIG. 2A) and the reference rodent muscle region 47 (FIG. 2A) are identified by the respective shaded portions 28 and 30, respectively. The y-axis is the proportion of each GL relative to the overall population of pixels in the studied segment (regions 38 and 47).

FIG. 3A shows that the tumor 38 and muscle regions 47 are clearly distinguishable by their different grey level values. The separable regions 28 and 30, due to the high contrast of the MRI scans obtained at the low magnetic field intensity.

In FIG. 3B, the grey level histograms for the tumor 41 and the reference rodent muscle region 48 are identified by the respective shaded portions 32 and 34, respectively.

In FIG. 3B, the pixel fractions are compared as a function of the Grey Level (GL) for the tumor 39 (FIG. 2B) and the reference muscle region 48 (FIG. 2B) of the rodent. In FIG. 3A, the grey level histograms for the tumor 38 and the reference rodent muscle region 47 are identified by the respective shaded portions 28 and 30, respectively.

FIG. 3B shows that the tumor and muscle regions are not clearly distinguishable by their different grey level values, due to the relatively low relative contrast of the MRI scans obtained at the high magnetic field intensity.

Reference is now made to FIGS. 4A and 4B, which compares the high resolution high-field MRI scan and the enhanced high resolution high-field scan, respectively, in accordance with a preferred embodiment of the present invention.

FIG. 4A shows the image 50 from the high-field scan and indicates regions of interest 52 and 54 as well as a reference region 56. FIG. 4B shows the results of scaling the image 40 (FIG. 2B) with the SF's determined from the low field and high field MRI scans. A tumor region 62, a white region 64 and a reference region 66 are clearly distinguishable and have a high level of contrast with the remaining portions of the image 60.

FIGS. 4A and 4B shows the contrast enhancement of the two regions, namely, the tumor region and the fat tissue region (white region).

Thus, using this method a clear image of rodent slice is obtained with the tumor and fatty region being well distinguished from other tissues imaged in the slice.

Figures 5A, 5C:
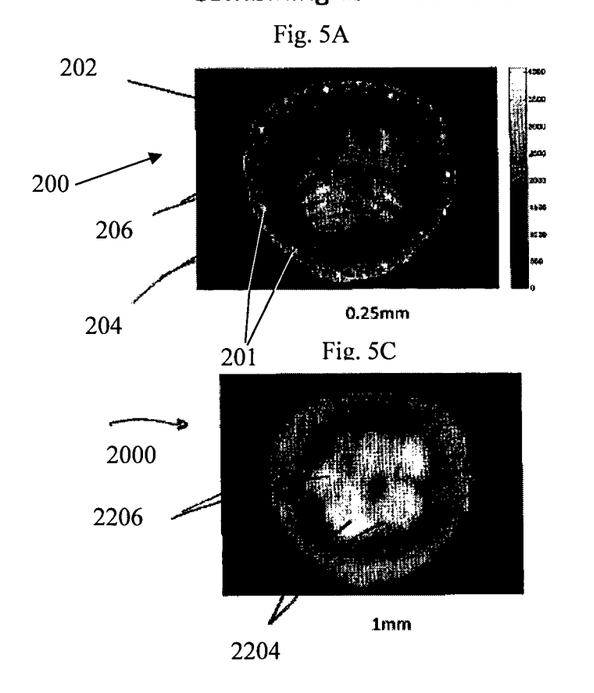
FIGS. 5A, 5B, 5C and 5D show MRI images of a cross sectional slice of a cucumber typically generated by the low intensity magnetic field device at different in-slice pixel sizes, respectively, in accordance with a preferred embodiment of the present invention.

Reference is now made to FIGS. 5A, 5B, 5C and 5D, which show MRI images of a cross sectional slice of a cucumber typically generated by the low intensity magnetic field device at different in-slice pixel sizes, respectively, in accordance with a preferred embodiment of the present invention;

FIG. 5A shows the cross section image of the cucumber 200 generated at an in-slice pixel size of 0.25 mm (high resolution) and a group of cucumber seeds 204 are clearly distinguishable from a cucumber background 202. However, due to the low SNR, the image of the cucumber seeds 204 is not clearly distinguishable from the cucumber background 202. A group of seeds 206 are not clearly distinguishable from the background 202. In addition, FIG. 5A shows a group of seeds 201 located on the periphery of the cucumber 200.

Figure 5B:
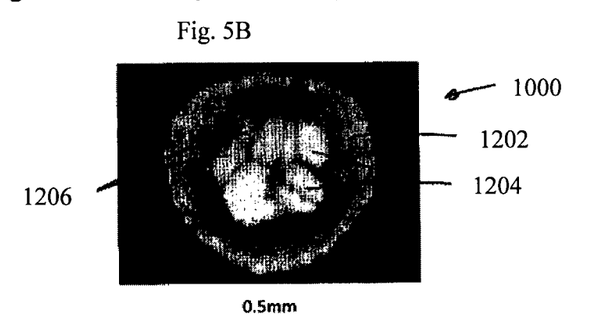

FIG. 5B shows a cross section image of the cucumber 1000 generated at an in-slice pixel size of 0.5 mm (medium resolution) and the group of seeds 1204 is clearly imaged. The image of the group of seeds 1206 is clearer. Due to edge effects, the border between the cucumber flesh 1202 and the group of cucumber seeds 1204 is not clearly defined. The group 206 is not clearly distinguishable from the cucumber background 202. Due to the decrease in the resolution, FIG. 5B does not clearly identify a group of seeds located on the periphery of the cucumber 1000.

FIG. 5C shows a cross section image of the cucumber 2000 generated at an in-slice pixel size of 1 mm (low resolution) and groups of cucumber seeds 2204 and 2206 are not clearly seen and the image is very blurred. Due to the further decrease in the resolution, FIG. 5C does not clearly identify a group of seeds located on the periphery of the cucumber 1000.

Figure 5D:
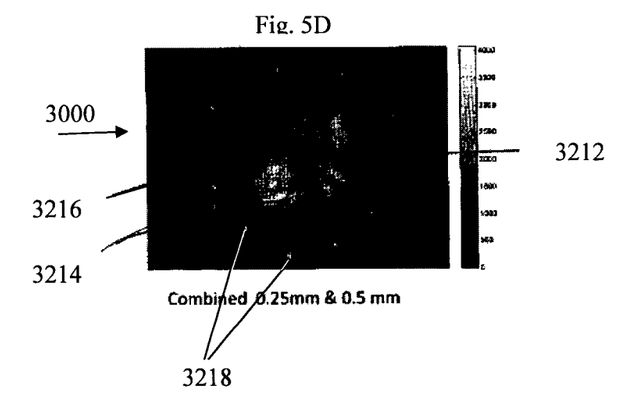

FIG. 5D shows a combined image 3000 of the high resolution (0.25 in-slice pixel size) and medium resolution (0.5 mm in-slice pixel size). The group of seeds 3214 is distinguishable from the cucumber background 3212 and the group of seeds 3216 is barely distinguishable from the cucumber background 3212. However, due to noise, the edges of the seeds 3214 and 3216 are not clearly discernible. FIG. 5D shows a group of seeds 3218 located on the periphery of the cucumber 3000. To summarize the resolution in 3000 in FIG. 5D has the full resolution of cucumber 200 in FIG. 5A.

Figure 6:
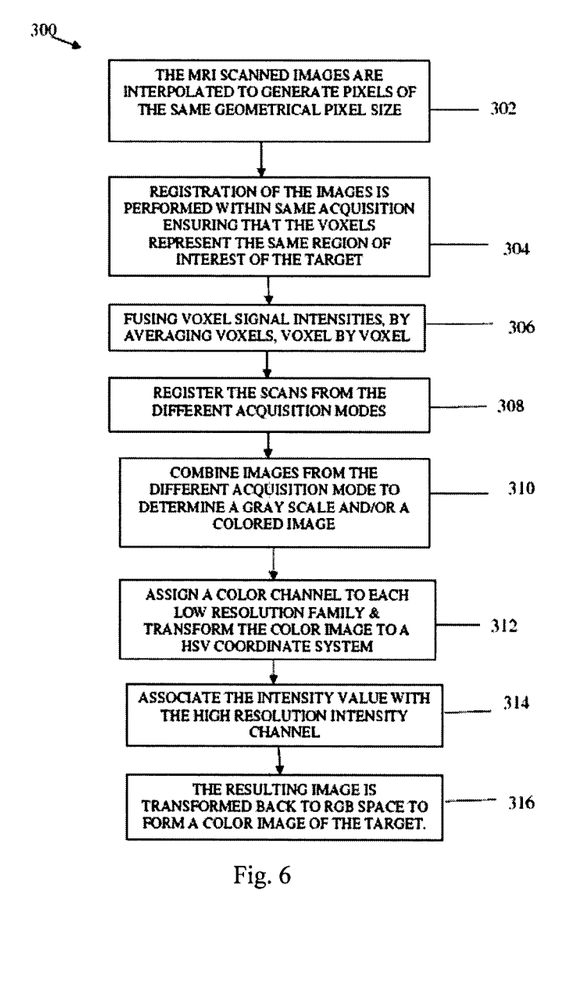
FIG. 6 present a flow chart of a typical procedure for fusing multiple sets of images of a given volume of the target into a single enhanced image, in accordance with a preferred embodiment of the present invention, and FIGS. 7A-7C compare in grey and color, the results of combining multi-resolutions images as grey and color images, in accordance with a preferred embodiment of the present invention.

Reference is now made to FIG. 6, which presents a flow chart of a typical procedure 300 for fusing multiple sets of images of a given volume of the target 14, into a single enhanced image, in accordance with a preferred embodiment of the present invention. The procedure 300 is controlled by the processing unit 23, wherein the images are taken at the same slice of the target 14.

In step 302, the MRI scanned images are interpolated in order to generate voxels of the same geometrical voxel size, as is known in the art.

In step 304, registration of the images acquired from the same acquisition mode is performed. The registration procedure ensures that the voxel representations of the images to be fused represent the same region of interest of the target.

In step 306, the registered images are averaged to form a single image for each acquisition mode. This image includes a multiplicity of slices.

In step 308, the combined images from the distinct acquisition modes used to image the registered target. A typical registration method is "The Lukas-Kanade Optical Flow Method", as is known in art and described in "An Iterative Image Registration Technique with an Application to Stereo Vision", B. D. Lucas and T. Kanade (1981), published in the Proceedings of Imaging Understanding Workshop, pages 121-130. Since the distinct image acquisition modes may have a different appearance, other methods known in the art for registering multi-modality images may be used. These can be based on maximizing mutual information of images patches as is known in the art.

In step 310, the registered MR images of different acquisition modes are fused according to any of the well know fusion methods. In the following steps of FIG. 6, a method that is suited to variable resolution images acquisitions is outlined:

In order to fuse the different acquisition modes of averaged images, they are divided into two types: high resolution images and low resolution images. The high resolution images are combined to form a single monochrome image as follows:

The pixel values are combined using some weighting which can be assigned by a variety of methods, such as a principal component analysis. The method is known in the art and described in "*Principal Component Analysis*", by I. T. Jolliffe, Series: *Springer Series in Statistics,* 2nd ed., Springer, N.Y., 2002, XXIX, 487 p. 28 illus. ISBN 978-0-387-95442-4. This combined monochrome image controls the brightness and/or intensity of the fused colored image while the low resolution images will control the spectral resolution of the fused image.

The steps for fusing these high resolution and low resolution images to colored image are further outlined in FIG. 6.

In step 314, each low-resolution image acquisition mode is assigned a color channel: for example, red, green and blue for three acquisition modes. The low resolution image is transformed to the HSV (hue, saturation, value) basis.

In step 318, the intensity channel (value) is associated with the high resolution monochrome image and/or combined with the low-resolution intensity channel, for example by the Brovey method, as is known in the art.

In step 320, the resulting image is transformed back to RGB space to form a colored fused final image of the target.

Figure 7A:
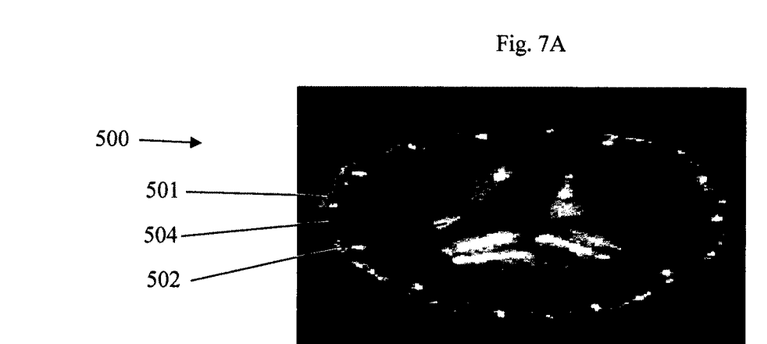
Figure 7B:
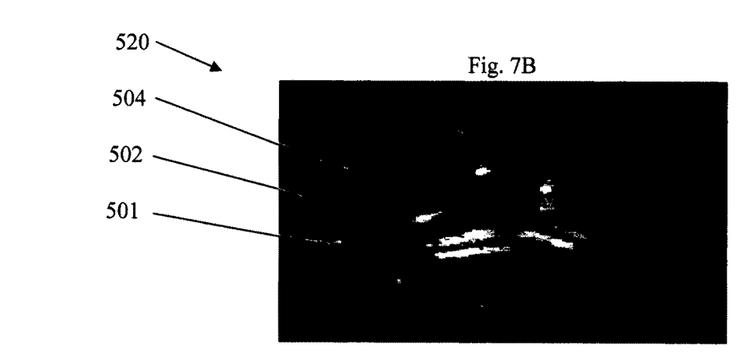
Figure 7C:
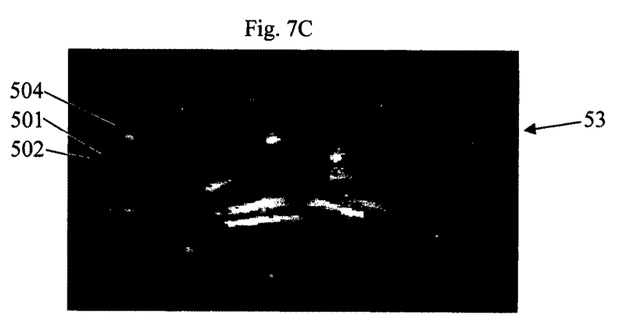

Reference is now made to FIGS. 7A-7C, which compare in grey and color, the results of combining multi-resolutions images as grey and color images, in accordance with a preferred embodiment of the present invention.

FIG. 7A shows a high resolution image 500 of a cross section of a cucumber 501 and groups of cucumber seeds 502 and 504. FIG. 7A is similar to the high resolution scan shown in FIG. 5A.

FIG. 7B shows a high resolution image 520 of a cross section of the cucumber 501 and groups of cucumber seeds 502 and 504. In the image 510, the high resolution image (FIG. 5A), the medium resolution image (FIG. 5B) and the low resolution image (FIG. 5C) are combined by a IHS method as described in "Application of the IHS Color Transform to the Processing of Multisensor Data and Image Enhancement", (Haydn, R., Dalke, G. W. and Henkel, J.:. Proc. of the International Symposium on Remote Sensing of Arid and Semiarid Lands, Cairo, pp. 599-616, 1982.), The image 520 is clearer than the colored image 510.

FIG. 7C shows a high resolution image 520 of a cross section of the cucumber 501 and groups of cucumber seeds 502 and 504. In the image 520, the high resolution image (FIG. 5A), the medium resolution image (FIG. 5B) and the low resolution image (FIG. 5C) are combined by the Brovey method, as is known in the art (step 314, FIG. 6). The image 530 clearly distinguishes between the groups of cucumbers 502 and 504 and the groups of cucumbers 502 and 504 are clearly distinguishable from the cucumber background. 501.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A magnetic resonance imaging (MRI) scanning assembly, comprising:
   a MRI scanning device operating at a first magnetic field intensity and generating a first plurality of MRI images of a target;
   the MRI scanning device operating at a second magnetic field intensity and generating a second plurality of MRI images of said target; and
   a processing unit configured to:
      identify at least two regions of interest in said first plurality of said MRI images,
      determine a monochrome level scaling factor between said at least two identified regions of interest, said monochrome level scaling factor is selected from a grey level, a red scale, green scale, and a blue scale,
      fuse said first plurality of MRI images and second plurality of MRI images based on the monochrome level scaling factor to generate a clear image representation of at least a portion of said target.

2. The MRI scanning assembly according to claim 1, wherein said first magnetic field intensity is less than 1.5 Tesla and said second magnetic field intensity is greater than 5 Tesla.

3. The MRI scanning assembly according to claim 1, further comprising at least one selected from a group consisting of (a) an MRI selector for selecting said MRI scanning device; (b) an image display unit for generating and displaying said at least said portion of said target.

4. A method for fusing MRI images of a target comprising:
- receiving a first plurality of MRI images of a target, said first plurality of MRI images generated by a MRI scanning device at a first magnetic field intensity;
- receiving a second plurality of MRI images of the target, said second plurality of MRI images generated by said MRI scanning device at a second magnetic field intensity;
- identifying at least two regions of interest in said first plurality of MRI images;
- determining a monochrome level scaling factor between said at least two identified regions of interest, said monochrome level scaling factor is selected from a grey level, a red scale, green scale, and a blue scale;
- fusing said first plurality of MRI images and said second plurality of MRI images based on the monochrome level scaling factor to generate a clear image representation of at least a portion of said target.

5. The method for fusing MRI images according to claim 4, wherein said first magnetic field intensity is less than 1.5 Tesla and said second magnetic field intensity is greater than 5 Tesla.

6. The method for fusing MRI images according to claim 4, wherein each one of said plurality of MRI images is associated with at least one member of a group of MRI device parameters.

7. The method for fusing MRI images according to claim 6, wherein said group of MRI device parameters is selected from the group consisting of MRI scanning parameters and MRI scanning protocols and any combination thereof and wherein said group of MRI scanning parameters comprises at least one of the following: pixel size and dwell time and said group of MRI scanning protocols comprises at least one of the following protocols: T1-weighted scan protocols and T2-weighted scan protocols.

8. The MRI scanning device according to claim 1, wherein said target is selected from comprises food products or industrial products.

9. The MRI scanning device according to claim 1, wherein said MRI scans comprise MRI scans for searching and investigating fluids.

10. The method for fusing MRI scans according to claim 4, wherein target is selected from food products or industrial products.

11. The MRI scanning assembly according to claim 1 wherein said target is selected from the group consisting of a group of cancerous cell, at least one anatomical organ, at least one cancerous anatomical organ and any combination thereof.

12. The method for fusing MRI scans according to claim 4 wherein said target is selected from the group consisting of a group of cancerous cell, at least one anatomical organ, at least one cancerous anatomical organ and any combination thereof.

* * * * *

UNITED STATES PATENT AND TRADEMARK OFFICE
CERTIFICATE OF CORRECTION

| | |
|---|---|
| PATENT NO. | : 9,720,065 B2 |
| APPLICATION NO. | : 13/877553 |
| DATED | : August 1, 2017 |
| INVENTOR(S) | : Uri Rapoport |

It is certified that error appears in the above-identified patent and that said Letters Patent is hereby corrected as shown below:

In the Specification

Column 1, immediately after the Title, Line 6, please insert the following paragraph:
-- CROSS-REFERENCE TO RELATED APPLICATIONS
This application is a National Phase Application of PCT International Application No. PCT/IL2011/00795, filed on October 6, 2011, published on April 12, 2012 as WO 2012/046241, which in turn claims priority from U.S. Provisional Patent Application No. 61/390,196, filed October 6, 2010, all of which are incorporated herein by reference in their entirety. --

Please replace the paragraph in Column 9, Line 56 with the following rewritten paragraph:
-- In step 312, each low-resolution image acquisition mode is assigned a color channel: for example, red, green and blue for three acquisition modes. The low resolution image is transformed to the HSV (hue, saturation, value) basis. --

Please replace the paragraph in Column 9, Line 60 with the following rewritten paragraph:
-- In step 314, the intensity channel (value) is associated with the high resolution monochrome image and/or combined with the low-resolution intensity channel, for example by the Brovey method, as is known in the art. --

Please replace the paragraph in Column 9, Line 64 with the following rewritten paragraph:
-- In step 316, the resulting image is transformed back to RGB space to form a colored fused final image of the target. --

Signed and Sealed this
Second Day of January, 2018

Joseph Matal
*Performing the Functions and Duties of the
Under Secretary of Commerce for Intellectual Property and
Director of the United States Patent and Trademark Office*